(12) United States Patent
Tu et al.

(10) Patent No.: US 8,955,231 B2
(45) Date of Patent: Feb. 17, 2015

(54) EXTENSOMETER FOR MEASURING HIGH-TEMPERATURE STRUCTURAL DEFORMATIONS BY MAGNIFICATION

(75) Inventors: Shandong Tu, Shanghai (CN); Jiuhong Jia, Shanghai (CN); Xiaoyin Hu, Shanghai (CN); Fuzhen Xuan, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 0 days.

(21) Appl. No.: 13/817,130

(22) PCT Filed: Sep. 28, 2011

(86) PCT No.: PCT/CN2011/080256
§ 371 (c)(1),
(2), (4) Date: Feb. 14, 2013

(87) PCT Pub. No.: WO2013/044455
PCT Pub. Date: Apr. 4, 2013

(65) Prior Publication Data
US 2014/0196296 A1   Jul. 17, 2014

(51) Int. Cl.
G01B 5/30 (2006.01)
G01B 7/16 (2006.01)
G01B 5/20 (2006.01)
G01N 3/06 (2006.01)
G01N 3/60 (2006.01)

(52) U.S. Cl.
CPC .. G01B 5/20 (2013.01); G01B 5/30 (2013.01); G01N 3/062 (2013.01); G01N 3/60 (2013.01)
USPC ............................................. 33/787; 73/286

(58) Field of Classification Search
CPC .............. G01B 5/30; G01B 7/16; G01B 7/24; G01B 7/22; G01B 11/16; G01B 5/0011; G01N 2203/0605; G01N 2203/0682; G01N 3/08; G01N 3/06; G01N 17/00; G01N 3/18; G01N 25/16

USPC ............................... 33/787–790; 73/826, 781
See application file for complete search history.

(56) References Cited

U.S. PATENT DOCUMENTS

| | | | | |
|---|---|---|---|---|
| 4,879,906 A | * | 11/1989 | Meline et al. | 33/787 |
| 4,884,456 A | * | 12/1989 | Meline et al. | 33/787 |
| 5,699,624 A | * | 12/1997 | Gaus et al. | 33/787 |
| 5,819,428 A | * | 10/1998 | Meyer | 33/787 |
| 6,907,677 B1 | * | 6/2005 | Hartman | 33/787 |
| 2014/0196296 A1 | * | 7/2014 | Tu et al. | 33/556 |

* cited by examiner

*Primary Examiner* — Yaritza Guadalupe-McCall
(74) *Attorney, Agent, or Firm* — Blue Filament Law PLLC; Avery N. Goldstein

(57) ABSTRACT

The present invention relates to an extensometer for measuring high-temperature structural deformations by magnification, the structure of the extensometer is that: two mounting block assemblies are mounted at the planar ends of two extension bars respectively, the top ends of the extension bars are connected tightly with the surface of a test piece, two connecting pieces are mounted at the inner sides of the two mounting block assemblies respectively, a deformation magnifying mechanism and a sensor bracket are mounted on the connecting pieces, a sensor is mounted on the sensor bracket, two connecting pieces are mounted on a same straight line, and the straight line is parallel to a straight line at which the top ends of the two extension bars are located, so as to ensure that the deformation of the test piece is delivered equally to the deformation magnifying mechanism on the connecting pieces. The present invention can measure local deformations of various metal and non-metallic structures online for a long time in real time at high temperatures, extend the deformation of the test piece at high temperatures outside of the high temperature region, and measure the deformations after they are magnified through a mechanical magnifying mechanism, thus the present invention has a very high linearity, resolution, and accuracy, meanwhile has a light structure and a small size, and is easy to install.

6 Claims, 5 Drawing Sheets

EXTENSOMETER FOR MEASURING HIGH-TEMPERATURE STRUCTURAL DEFORMATIONS BY MAGNIFICATION

FIELD OF TECHNOLOGY

The present invention relates to the technical field of measurement, especially to the technical field of measuring structural and material deformations, in particular to an extensometer for measuring high-temperature structural deformations by magnification, this extensometer can measure local deformations of materials and structures online in real time at high temperatures.

DESCRIPTION OF RELATED ARTS

As the energy and environmental issues become increasingly prominent, efficient and energy-saving concepts began to lead design and manufacture and operation and maintenance of process industrial devices, resulting in that the process industrial devices of petroleum, chemical industry, electric power, metallurgy, and so on develop towards the trend of high temperature, high pressure and large-scale. The pressure vessels and pipes used by these industries are often in high temperature environments for long-terms, and would have inevitably unrecoverable deformations under high temperatures, causing disintegration of mechanical properties and physical properties of materials, threatening seriously the achievement of security, reliability and economic goals of the entire process industry,. Therefore, in order to ensure security of high temperature and high pressure process devices, and to avoid unnecessary stopping, monitoring security of devices has attracted wide attentions. In high-temperature, high-pressure environments, the deformation measurement is the most direct and reliable monitoring method to ensure structural safety. In high temperature environments simulated in laboratories, the accurate measurement of local deformations of test pieces is also a basis to study the laws of high temperature material deformations and damages.

However, designing deformation sensing devices with high accuracy and high reliability is a key to achieve measuring deformations for a long time under high temperatures. In order to solve this problem, domestic and foreign scholars have designed some sensing devices, such as the strain follower of U.S. Pat. No. 4,936,150, the high-frequency response high-temperature pull-torsion fatigue extensometer of Chinese patent CN200410072189.1 and the strain testing device for pull-torsion fatigue experiments in corrosive environments of Chinese patent CN200910054544.5, these sensing devices can only monitor standard test pieces in laboratories. In order to meet the industrial application requirements, the extension type sensing device for high temperature components' deformations of CN200910045657.9 is newly designed, although this device can monitor effectively local deformations of pipes, its accuracy is yet unsatisfactory during the application.

SUMMARY OF THE INVENTION

Aspects of the present invention generally pertain to an extensometer for measuring high-temperature structural deformations by magnification which has laboratory and engineering application values, and can measure surface deformations of different high temperature members or test pieces. This extensometer is lightweight, has a good stability, is convenient to install and has a long service life and a high measurement accuracy.

The present invention is realized through the following technical solutions:

An extensometer for measuring high-temperature structural deformations by magnification is characterized in that the extensometer for measuring high-temperature structural deformations by magnification is consisted of a pair of extension bars, two mounting block assemblies, two connecting pieces, a deformation magnifying mechanism, a sensor and a sensor bracket, the extension bar is a round bar, one end of which is planar, the other end of which is tapered; the mounting block assemblies are fixed at the planar ends of the extension bars by inserting mounting screws into mounting holes, respectively; the mounting block assembly includes a first mounting block and a second mounting block, a circular extension bar mounting surface is arranged at the middle part of the contacting interface between the first mounting block and the second mounting block, four mounting holes are arranged on the extension bar mounting surface respectively, one side of the second mounting block has a first semi-circular boss, at the middle part of which is arranged a first fixing hole; one end of the connecting piece is a second semi-circular boss, inside which is arranged a second fixing hole, the connecting piece and the second mounting block are fixed by inserting the mounting screws into the first fixing holes and the second fixing holes, the other end of the connecting piece is a cuboid, inside which are arranged two fixing grooves, the deformation magnifying mechanism and the sensor bracket are mounted in the fixing grooves; the deformation magnifying mechanism is a stepped symmetrical square cylinder with constant width, four flexible hinges are arranged symmetrically at the junctions of steps and the middle part of the cylinder, and form an arch bridge-shaped structure, two mounting holes are arranged at each of two ends of the deformation magnifying mechanism, so as to mount the deformation magnifying mechanism on the connecting pieces, the vault of the arch bridge-shaped structure is downward, the midpoint of the deformation magnifying mechanism acts as an output end, the sensor is mounted on the sensor bracket, perpendicular to the deformation magnifying mechanism and connected to a test terminal.

In the above-mentioned technical solution, the two connecting pieces are mounted on a same straight line, and the straight line is parallel to a straight line at which the top ends of the two extension bars are located, so as to ensure that the deformation of a test piece is delivered equally to the deformation magnifying mechanism on the connecting pieces.

In the above-mentioned technical solution, the angle between the connecting piece and the mounting block assembly can be adjusted within the range that is >0° and ≤90°, so as to achieve the installation on test pieces with different surface shapes such as a plane, a curved surface and so on.

In the above-mentioned technical solution, the mounting position of the deformation magnifying mechanism in the fixing grooves can be adjusted, so as to meet the requirements of different spans to be measured.

In the above-mentioned technical solution, the deformation of the surface of a component to be measured is delivered by the extension bars, magnified mechanically by the deformation magnifying mechanism and then measured by the sensor. The flexible hinges used in the deformation magnifying mechanism can be geometric structures such as round type, oval type, filleted straight beam type, parabolic type or hyperbolic type.

In the above-mentioned technical solution, the sensor can be a LVDT displacement sensor, a displacement sensor, an eddy current sensor, a laser displacement sensor or the like.

In the above-mentioned extensometer, when the working environment is more complicated and it should take a long time to measure high-temperature structures, fixing block assemblies 19 can be adopted to weld the extensometer to the surface of a test piece; when it works in a laboratory environment, very light flexible high temperature resistant ceramic fiber ropes 21 can be adopted to fix the extensometer on the test piece (the component to be measured).

The advantages of the present invention are as follows

1. The present invention can measure local deformations of various structures online in real time at high temperatures, the surface temperature of the component to be measured can be up to 1200° C., and the present invention has a high measurement accuracy, a very high linearity and a very high resolution, the test results are accurate, reliable and repeatable.

2. The present invention is applicable to structures with different surface shapes, can meet requirements of different spans, has a small size and a light weight, can adapt to a variety of working conditions, and has a wide range of applications;

3. The present invention introduces the deformation magnifying mechanism composed of flexible hinges, and has characteristics such as no friction, no lubrication needed, compact, no maintenance needed, virtually no assembly needed and so on.

4. The present invention introduces the deformation magnifying mechanism, to measure the deformation after magnifying the deformation mechanically, greatly improving the resolution and the reliability of the extensometer.

5. For heat insulating materials can be filled between the sensing component and the component to be measured, and the extension bars are made from materials with smaller thermal conductivity, the sensor is separated from the high temperature environment, greatly improving the working environment of the sensing component, extending the service life of the extensometer for measuring high-temperature structural deformations by magnification, and having a very high practical application value.

BRIEF DESCRIPTION OF THE DRAWINGS

In FIG. 1: 1 the sensor, 2 the clip, 3 the sensor bracket, 4 the connecting piece, 5 the mounting block assembly, 6 the deformation magnifying mechanism, 7 the extension bar, 8 the component to be measured, 9 the test terminal.

In FIG. 2: 4 the connecting piece, 5a the mounting block I, 5b the mounting block II, 10 the mounting screw, 11 the mounting surface of the extension bar, 12 the mounting hole, 13a the fixing hole, 13b the fixing hole, 14 the fixing groove.

In FIG. 3: 1 the sensor, 2 the clip, 3 the sensor bracket, 4 the connecting piece, 5a the mounting block I, 5b the mounting block II, 6 the deformation magnifying mechanism, 7 the extension bar, 15 the mounting bolt.

In FIG. 4: 16 the mounting hole, 17 the flexible hinge, 18 the output end.

In FIG. 6: 10 the mounting screw, 19a the fixing block I, 19b the fixing block II.

In FIG. 7: 20 the sensor, 21 is the component to be measured, 22 the ceramic fiber rope.

In FIG. 10: 24 the extension device already possessed by the laboratory, 25 the aperture.

DETAILED DESCRIPTION OF THE PREFERRED EMBODIMENT

Figure 1:
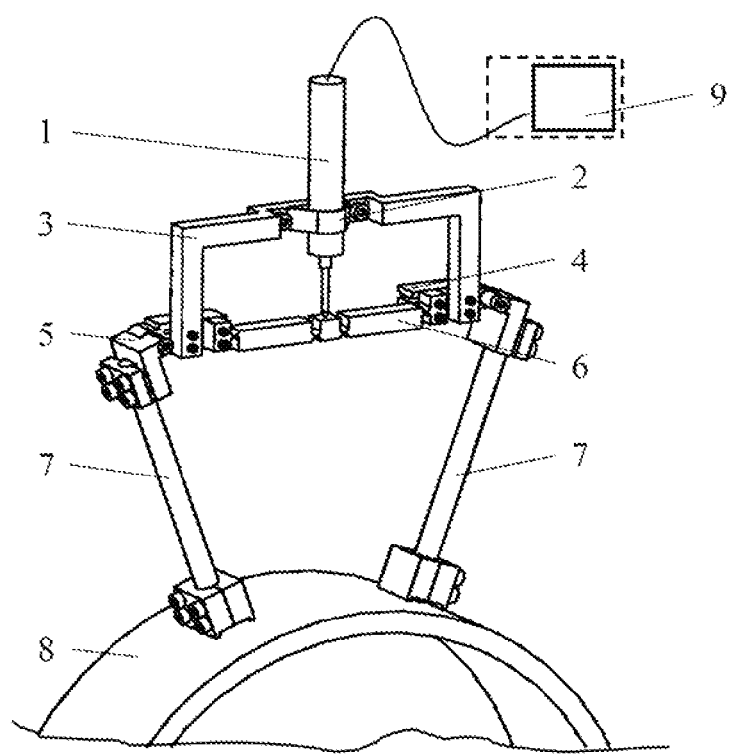
FIG. 1 is a schematic view of the present invention.

The present invention is further exemplified hereinafter by reference to the accompanying drawings and the following embodiments.

The extension bar 7 adopts zirconia ceramic materials with high temperature resistance and low thermal coefficient. The clip 2, the sensor bracket 3, the connecting piece 4, the mounting block assembly 5 all adopt lightweight aluminum alloy materials. The deformation magnification mechanism 6 adopts AL7075 having a smaller elastic modulus and a higher strength. When a heat insulating material is filled between the sensing component and the component to be measured, the lengths of the two extension bars 7 both are greater than the thickness of the insulating material, to ensure that the mounting mechanism, the connecting mechanism, the magnifying mechanism and the sensor all work outside of the insulating layer of the component to be measured. When it takes a long time to measure a high temperature structure, fixing block assemblies 19 should be used. The fixing block assembly 19 adopts high temperature resistant material, whose thermal expansion coefficient is close to that of the material adopted by the component to be measured, to prevent the extensometer from dropping off during a long-term work. When the extensometer works in a laboratory environment, very light high temperature resistant flexible ceramic fiber ropes 22 can be adopted to fix the extensometer on the test piece.

Figure 2:
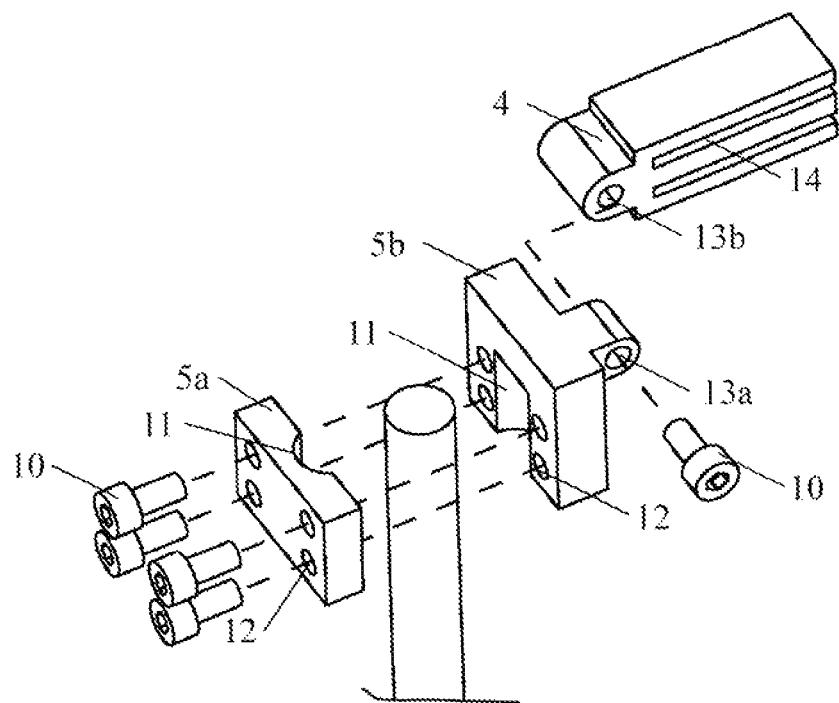
FIG. 2 is a schematic view of the installation of the mounting block assembly and the connecting piece.
Figure 3:
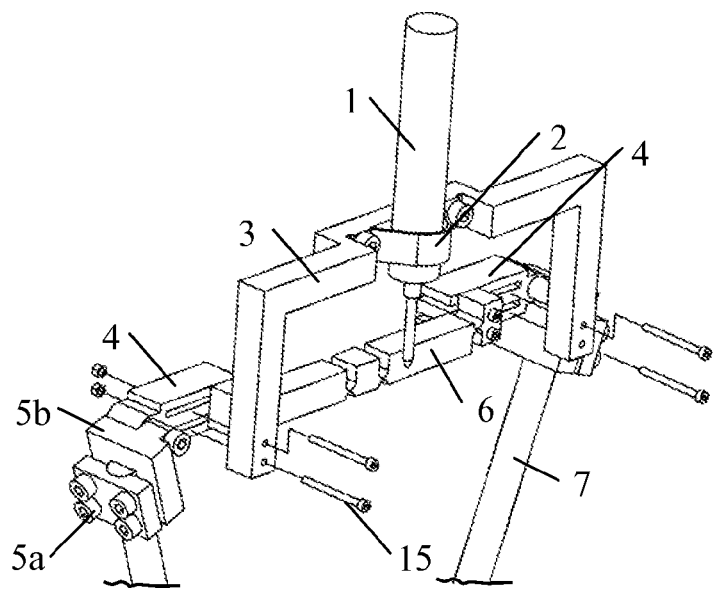
FIG. 3 is a schematic view of the installation of the sensor bracket 3.
Figure 6:
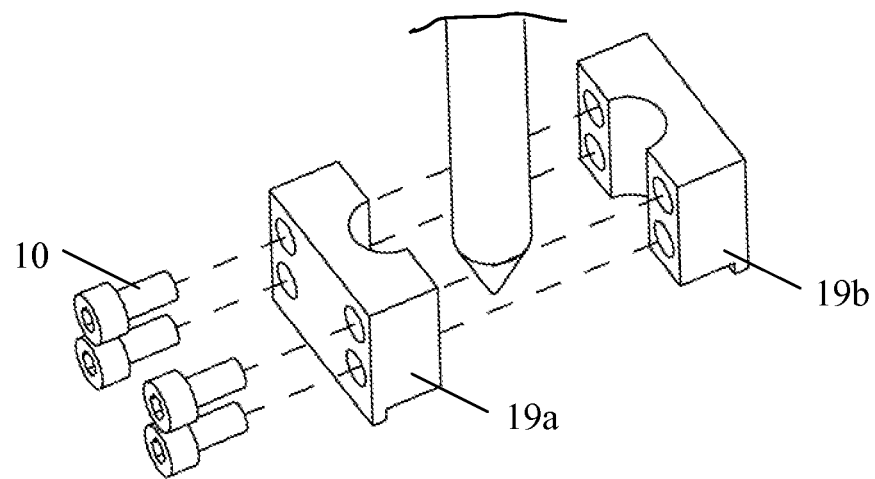
FIG. 6 is a schematic view of the installation of the fixing block assembly 19.
Figure 7:
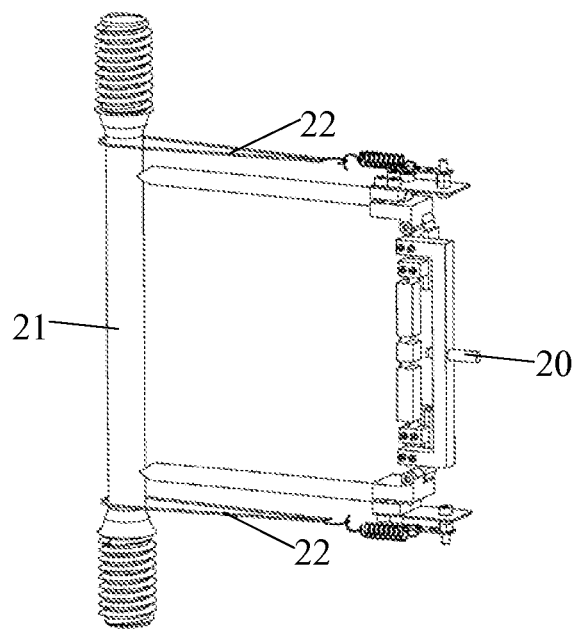
FIG. 7 is a schematic view of fixing the present invention on the component 21 to be measured with two ceramic fiber ropes.

When the extensometer is installed, firstly the mounting block assemblies 5 are mounted on the planar ends of the extension bars 7, and then the connecting pieces 4 are mounted on the second mounting blocks 5b, as shown in FIG. 2. Then the deformation magnifying mechanism 6 and the sensor bracket 3 are mounted on the connecting pieces 4, the sensor 1 is mounted on the sensor bracket 3, and the convex portion of the deformation magnifying mechanism 6 is downward, as shown in FIG. 3. Finally, the extensometer is fixed on the component to be measured with the fixing block assemblies 19 (FIG. 6) or the ceramic fiber ropes 22 (FIG. 7).

Figure 4:
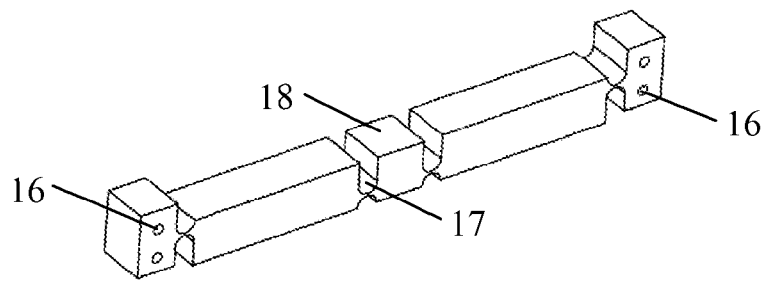
FIG. 4 is a schematic view of the structure of the deformation magnifying mechanism 6 in the present invention.
Figure 5:
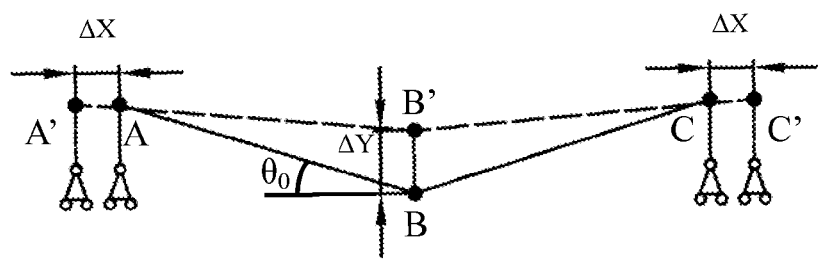
FIG. 5 is a schematic simplified view of the structure of the deformation magnifying mechanism in the present invention

The working principle of the extensometer is that: when the component to be measured deforms, the deformation is extended by the extension bars 7, and converted into the change of the horizontal distance between the two connecting pieces 4. The deformation $\Delta X$ extended is delivered to the deformation magnifying mechanism 6, which is equivalent to applying a displacement load $\Delta X$ in the horizontal direction to two ends of the deformation magnifying mechanism 6. The deformation magnifying mechanism 6 has a structure shown in FIG. 4, and is consisted of four flexible hinges 17, and has an output end 18 located at the middle position of the deformation magnifying mechanism 6, two ends of which are connected with two square cylinders through two flexible hinges 17, respectively, and then the two square cylinders are connected with two mounting ends through two flexible hinges 17, two mounting holes 16 are arranged on each of the two mounting ends, and the structure of the output end 18 being connected with the two square cylinders through two flexible hinges 17 projects two mounting ends, to form a stepped systemically square cylinder. Points A, C are used to represent the hinges 17 at the two ends under the initial condition, respectively, B represents the output end, as shown in FIG. 5. After loaded, the flexible hinges 17 in the deformation magnifying mechanism 6 deform, the flexible hinges 17 at the two ends of the deformation magnifying mechanism 6 moves to the points A', C', the output end 18 moves to the point B'. The output displacement ΔY of the output end 18 is higher than the load ΔX in the horizontal direction, the ratio of them ΔY/2ΔX is the magnification factor of the deformation magnifying mechanism 6. The magnification factor of the deformation magnifying mechanism 6 is a constant, and would not vary with changes of input quantities. The output value of the deformation magnifying mechanism 6 is delivered to the sensor 1.

Embodiment 1

By simulating the condition of the main steam pipe of a petrochemical factory, the present invention is tested to measure a local deformation of the main steam pipe. The main parameters of the main steam pipe is that: the material is 10CrMo910, the pressure is 10 MPa, the temperature is 540° C., the specification is Φ273×28 mm, the thickness of the insulating layer is 100 mm. The extension bars 7 used in the test is 150 mm in length. In order to make the extensometer be able to be fixed stably to the surface of the pipe to be measured, a pair of fixing block assemblies 19 (respectively indicated by 19a and 19b) are adopted, and fixed to the surface of the pipe to be measured by spot welding.

Figure 8:
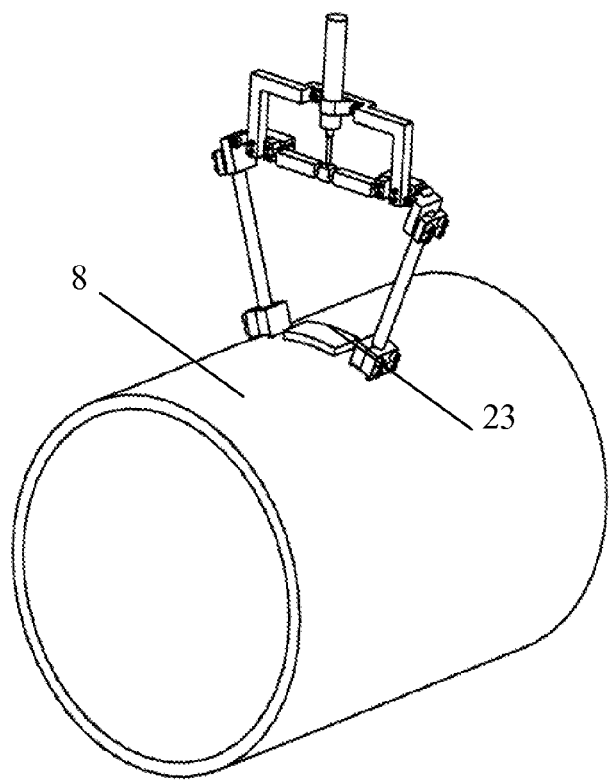
FIG. 8 is a schematic view of the installation of the experiment 1 of the present invention.

When the extensometer is installed, the insulating layer of the pipe is removed, and the extensometer is fixed on the pipe after the mounting position is polished and cleaned. The installation is carried out according to the operation steps in the process of the embodiment. In order to check the accuracy of the extensometer, a high temperature strain gauge 23 (KHCM-10-120-G15-11C2M) is mounted at the middle of the two fixing block assemblies 19, as shown in FIG. 8, the measuring data of the strain gauge is compared with those of the extensometer. The present invention and the strain gauge are connected with a data acquisition module and a computer respectively, the initial position in the data acquisition system is reset, and the preparatory work has been completed.

The online monitoring period of the extensometer for measuring high-temperature structural deformations by magnification is six months.

Figure 9:
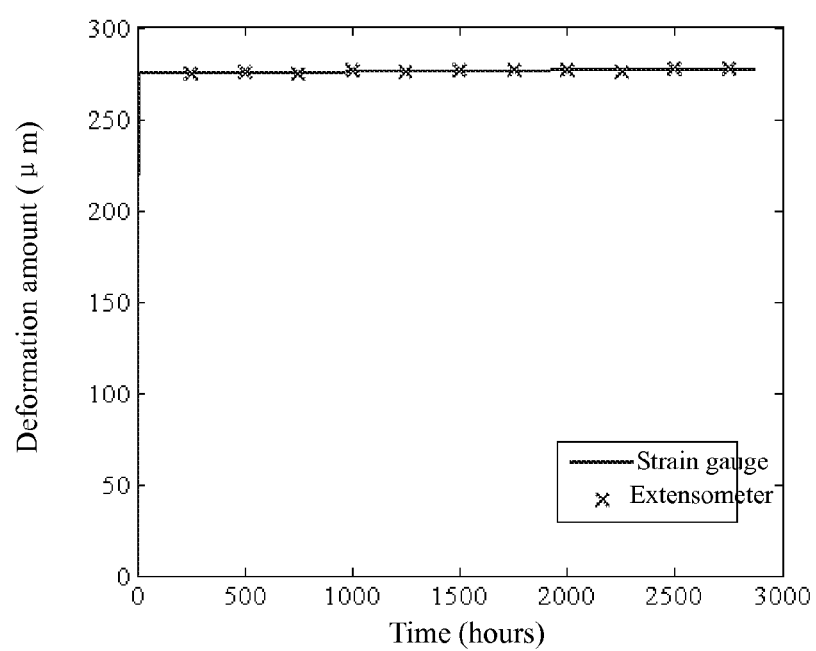
FIG. 9 is a schematic view of the comparison of the measuring results of the present invention and the high temperature strain gauge 23.

The results of the implementation:

The present invention obviously monitored the deformation of the main steam pipe during the pipe running period. Through the comparison of the data measured by the present invention and the strain gauge 23, it is found that the present invention can measure the deformation of the component to be measured after the deformation is magnified 5 times, and there is no distortion in the whole process. The data measured by the present invention are divided by the magnification factor of 5, and then compared with the data measured by the strain gauge 23, and it is found that the accuracy of the present invention is higher, and can reach ±0.2 μm, the resolution reaches 0.2 μm, as shown in FIG. 9, which can prove that the extensometer can meet the requirements of monitoring online the main steam pipe.

Embodiment 2

Figure 10:
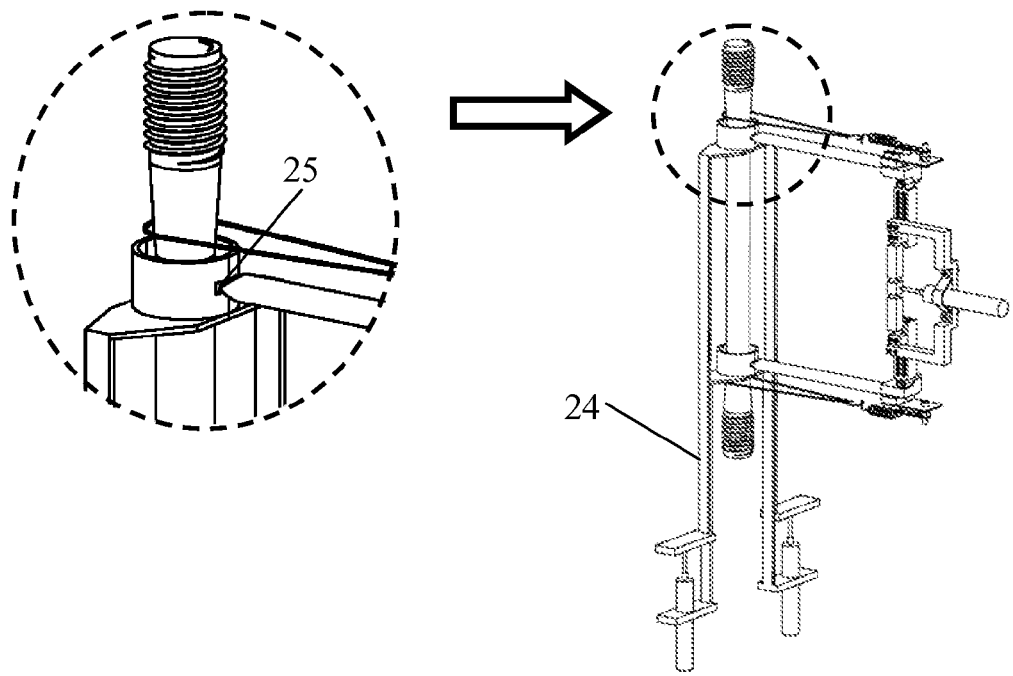
FIG. 10 is a schematic view of the installation of the experiment 2 of the present invention.

In order to verify the accuracy and reliability of the extensometer invented in the laboratory, the extensometer and the extension device 24 of the INSTRON company processed by the laboratory are simultaneously installed on a creep test piece of an electronic creep testing machine, as shown in FIG. 10, the measuring data of the existing extension device 24 is compared with those of the present invention. The extensometer is bound on the component to be measured with high temperature resistant ceramic fiber ropes 22, two circular holes 25 are arranged respectively at two clasps of the existing extension device 24, the conical top ends of the extension bars 7 are inserted into the circular holes 25 respectively.

The component 21 to be measured is a standard creep round bar test piece, the material is P92 steel, the experimental temperature is 600° C., the thickness of the insulating layer is 100 mm. the period of the creep test is 3600 hours.

During testing, the extension bar 7 used in the present invention is 150 mm in length.

Figure 11:
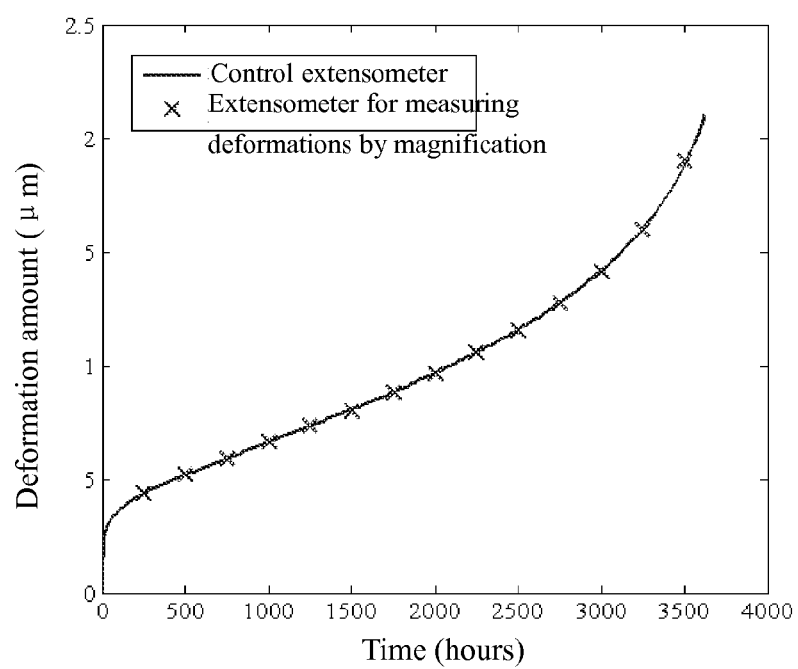
FIG. 11 is a schematic view of the comparison of the measuring results of the present invention and the extension device 24 already possessed by the laboratory.

The results of the implementation:

Through the comparison of the data measured by the extensometer for measuring high-temperature structural deformations by magnification of the present invention and the existing extension device 24, it is found that the present invention can measure accurately the deformation of the component to be measured after the deformation is magnified 5 times, and there is no malfunction an distortion in the whole process. The data measured by the present invention are divided by the magnification factor of 5, and then compared with the data measured by the existing extension device 24, as shown in FIG. 11, and it is found that, compared with the existing extension device 24 of the laboratory, the present invention has a higher accuracy and a higher resolution, up to ±0.2 μm and 0.2 μm respectively.

In the present specification, the present invention has been described according to the particular embodiments. But it is obvious that these embodiments can be modified or changed without departure from the spirit and scope of the present invention. Therefore, the specification and drawings described above are exemplary only and not intended to be limiting.

We claim:

1. An extensometer for measuring high-temperature structural deformations by magnification, characterized in that the extensometer for measuring high-temperature structural deformations by magnification is consisted of a pair of extension bars (7), two mounting block assemblies (5), two connecting pieces (4), a deformation magnifying mechanism (6), a sensor (1) and a sensor bracket (3), the extension bar (7) is a round bar, one end of which is planar, the other end of which is tapered; the mounting block assemblies (5) are fixed at the planar ends of the extension bars (7) by inserting mounting screws (10) into mounting holes (12), respectively; the mounting block assembly (5) includes a first mounting block (5a) and a second mounting block (5b), a circular extension bar mounting surface (11) is arranged at the middle part of the contacting interface between the first mounting block (5a) and the second mounting block (5b), four mounting holes (12) are arranged on the extension bar mounting surface (11) respectively, one side of the second mounting block (5b) has a first semi-circular boss, at the middle part of which is arranged a first fixing hole (13a); one end of the connecting piece (4) is a second semi-circular boss, inside which is arranged a second fixing hole (13b), the connecting piece (4)

and the second mounting block (5*b*) are fixed by inserting the mounting screws (10) into the first fixing holes (13*a*) and the second fixing holes (13*b*), the other end of the connecting piece (4) is a cuboid, inside which are arranged two fixing grooves (14), the deformation magnifying mechanism (6) and the sensor bracket (3) are mounted in the fixing grooves (14); the deformation magnifying mechanism (6) is a stepped symmetrical square cylinder with a constant width, four flexible hinges (17) are arranged symmetrically at the junctions of steps and the middle part of the cylinder, and form an arch bridge-shaped structure, two mounting holes (16) are arranged at each of two ends of the deformation magnifying mechanism (6), so as to mount the deformation magnifying mechanism (6) on the connecting pieces (4), the vault of the arch bridge-shaped structure is downward, the midpoint of the deformation magnifying mechanism (6) acts as an output end (18), the sensor (1) is mounted on the sensor bracket (3), perpendicular to the deformation magnifying mechanism (6) and connected to a test terminal (9).

2. The extensometer for measuring high-temperature structural deformations by magnification according to claim 1, characterized in that, the two connecting pieces (4) are mounted on a same straight line, and the straight line is parallel to a straight line at which the top ends of the two extension bars (7) are located, so as to ensure that the deformation of a test piece is delivered equally to the deformation magnifying mechanism (6) on the connecting pieces.

3. The extensometer for measuring high-temperature structural deformations by magnification according to claim 1, characterized in that, the angle between the connecting piece (4) and the mounting block assembly (5) can be adjusted within the range that is >0° and ≤90°, so as to achieve the installations on test pieces with different surface shapes.

4. The extensometer for measuring high-temperature structural deformations by magnification according to claim 1, characterized in that, the mounting position of the deformation magnifying mechanism (6) in the fixing grooves (14) can be adjusted, so as to meet the requirements of different spans to be measured.

5. The extensometer for measuring high-temperature structural deformations by magnification according to claim 1, characterized in that, the deformation of the surface of a component to be measured is delivered by the extension bars (7), magnified mechanically by the deformation magnifying mechanism (6) and then measured by the sensor (1).

6. The extensometer for measuring high-temperature structural deformations by magnification according to claim 4, characterized in that, the flexible hinges (17) used in the deformation magnifying mechanism (6) can be of round type, oval type, filleted straight beam type, parabolic type or hyperbolic type.

* * * * *